US009678011B2

(12) United States Patent
Nietner et al.

(10) Patent No.: US 9,678,011 B2
(45) Date of Patent: Jun. 13, 2017

(54) FLUORESCENT CONTACT IMAGING FOR IN-PROCESS PRINT SENSING

(71) Applicant: Massachusetts Institute of Technology, Cambridge, MA (US)

(72) Inventors: Larissa F. Nietner, Cambridge, MA (US); Scott T. Nill, Fort Wayne, IN (US); David E. Hardt, Concord, MA (US); Muhammad A. Hawwa, Dhahran (SA); Hussain Al-Qahtani, Dhahran (SA)

(73) Assignees: Massachusetts Institute of Technology, Cambridge, MA (US); King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/609,925

(22) Filed: Jan. 30, 2015

(65) Prior Publication Data
US 2015/0219559 A1 Aug. 6, 2015

Related U.S. Application Data

(60) Provisional application No. 61/934,903, filed on Feb. 3, 2014, provisional application No. 61/934,909, filed
(Continued)

(51) Int. Cl.
*G01N 21/64* (2006.01)
*B29C 59/16* (2006.01)
(Continued)

(52) U.S. Cl.
CPC ............ *G01N 21/64* (2013.01); *B29C 59/16* (2013.01); *G03F 7/0002* (2013.01); *B29L 2009/005* (2013.01); *G01N 2021/6497* (2013.01)

(58) Field of Classification Search
CPC ................................ G01N 21/64; B29C 59/16
See application file for complete search history.

(56) References Cited

U.S. PATENT DOCUMENTS 8,559,103 B2    10/2013   Hecker
8,765,215 B1 *   7/2014   Fitch .................. C23C 14/0015
                                                              427/162
(Continued)

FOREIGN PATENT DOCUMENTS

JP              069217 A        3/2007
JP         2007069217 A  *     3/2007
(Continued)

OTHER PUBLICATIONS

Notification of Transmittal of The International Search Report and the Written Opinion of the International Searching Authority for PCT/US2015/014060 mailed on Apr. 28, 2015.

*Primary Examiner* — David Porta
*Assistant Examiner* — Faye Boosalis
(74) *Attorney, Agent, or Firm* — Sam Pasternack; MIT Technology Licensing Office

(57) ABSTRACT

System for visualization of conformal contact. The system visualizes conformal contact between a patterned stamp and a transparent impression surface. A patterned stamp is provided that includes a fluorescent structure for contact with the impression surface. A source of UV light is provided for transmission through the transparent impression surface to interact with the fluorescent structure to generate visible light re-emitted by the fluorescent structure. An imaging system captures the visible light to form a high-contrast image of an area of conformal contact between the patterned stamp and the impression surface. The high-contrast image comprises bright and dark regions representing contact and no contact respectively.

8 Claims, 3 Drawing Sheets

Related U.S. Application Data on Feb. 3, 2014, provisional application No. 61/934,920, filed on Feb. 3, 2014.

(51) Int. Cl.
 *G03F 7/00* (2006.01)
 *B29L 9/00* (2006.01)

(56) References Cited

U.S. PATENT DOCUMENTS

| | | | |
|---|---|---|---|
| 2010/0108874 A1* | 5/2010 | Zahedi | B42D 25/355 250/271 |
| 2012/0021140 A1 | 1/2012 | Dijksman | |
| 2013/0106023 A1 | 5/2013 | Iimura | |

FOREIGN PATENT DOCUMENTS

| | | |
|---|---|---|
| JP | 296823 A | 11/2007 |
| JP | 2007296823 A * | 11/2007 |
| WO | 2012/022561 A1 | 2/2012 |
| WO | 2013092766 A1 | 6/2013 |

* cited by examiner bright contact dark no contact interference distance

UV Illumination

Image Carrier

Camera

Impression Roll

FLUORESCENT CONTACT IMAGING FOR IN-PROCESS PRINT SENSING

This application claims priority to provisional application Ser. No. 61/934,903 filed Feb. 3, 2014; Ser. No. 61/934,909 filed Feb. 3, 2014; and Ser. No. 61/934,920 filed Feb. 3, 2014, the contents of all of which are incorporated herein by reference.

BACKGROUND OF THE INVENTION

This invention relates to a system for the visualization of conformal contact between a patterned stamp and a transparent impression surface.

With the advent of printed electronics, printed photovoltaics, and printed engineered metasurfaces, there is a need to achieve feature resolutions finer than ever before in the printing industry, and to print these patterns reliably at low cost. Currently, inspection of the printing process is done in retrospect, downstream from the printing process. This approach results in a long delay between the printing and the inspection of the printed media, resulting in large amounts of scrap when the material doesn't meet specifications. In high-value printed media that uses precious ink or substrate, as with flexible electronics, waste can be quite costly. It is becoming increasingly desirable to have an inspection process that guarantees proper printing results as the point of printing and in real time.

Many common methods for contact imaging, comprising an illumination source and detector, require precise manipulation of the incident light in directionality, as is the case with total internal reflection (TIR) based methods, or control of the properties of the light, as with polarized illumination. Furthermore, the introduction of a substrate may interfere with the structuring of the illumination.

An object of the invention is therefore an imaging system for contact sensing having particular application in a roll-to-roll, continuous microcontact printing system.

SUMMARY OF THE INVENTION

In one aspect, the system of the invention for visualization of conformal contact between a patterned stamp and a transparent impression surface includes a patterned stamp, including a fluorescent structure, for contact with an impression surface. A source for ultraviolet (UV) light is provided for transmission through the transparent impression surface to interact with the fluorescent structure in the patterned stamp to generate visible light re-emitted by the fluorescent structure. An imaging system captures the visible light to form a high-contrast image of an area of conformal contact between the patterned stamp and the impression surface. In a preferred embodiment, the high-contrast image includes bright and dark regions representing contact and no contact respectively. The stamp may have a layered configuration including fluorescent particles or the stamp may include embedded fluorescent markers. The fluorescent structure may be flourescein.

The present invention has application to roll-to-roll microcontact printing and may include a transparent impression surface that is a cylinder.

BRIEF DESCRIPTION OF THE DRAWING

FIG. 1b is a cross-sectional view of the embodiment illustrated in FIG. 1a.

DESCRIPTION OF THE PREFERRED EMBODIMENT

The present invention uses a fluorescent stamp (image carrier), that may be layered, in conjunction with a transparent impression element to form a high-contrast image of the area of intimate contact between an image carrier, substrate and impression surface or the area of intimate contact between an image carrier and impression surface. In one embodiment, a stamp is loaded with dye (or particles) that fluoresce. A suitable material for the stamp is PDMS, which is a clear polymer. The dye may be a fluorescein or a chemical compound which fluoresces in the presence of UV light. The fluorescent structures within the stamp adsorb the incident UV and re-emit in the visible spectrum to be detected by an imaging system.

Figure 1A:
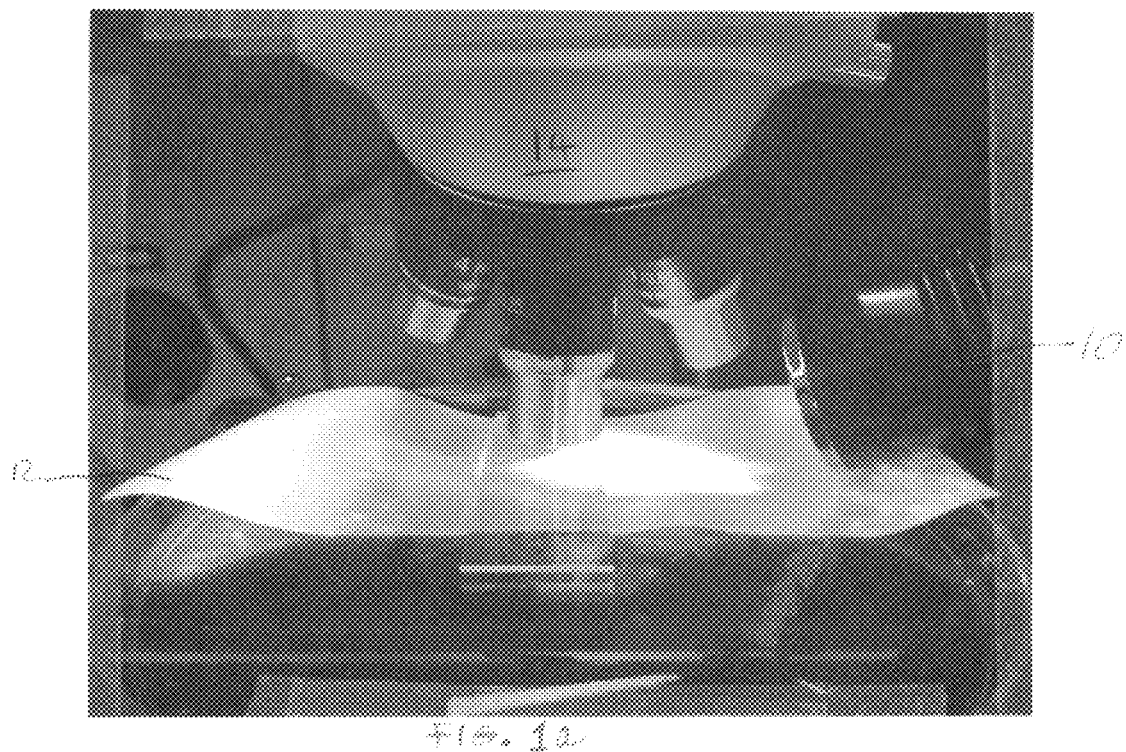
FIG. 1a is a perspective view of a fluorescent-doped stamp in partial contact with a transparent substrate.
Figure 1B:
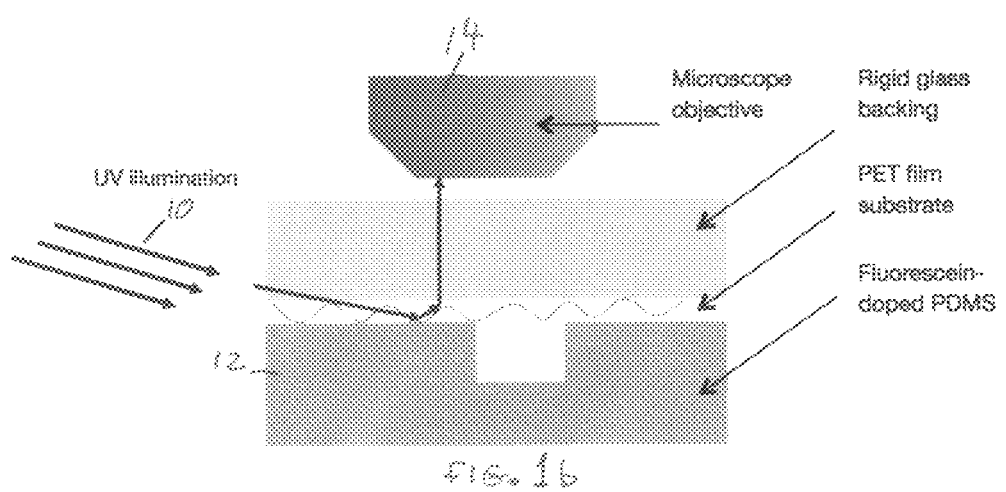

With reference to FIGS. 1a and 1b, a UV light source 10 illuminates a micropatterned stamp 12 that includes fluorescent material therein through a transparent impression surface. An imaging system 14 images the re-emitted light is the visible range.

The stamp 12 used in the present system is fabricated with fluorescent particles, preferably in a layered configuration as described in provisional application Ser. No. 61/934,903 incorporated by reference above. As discussed in that provisional application, a layer in the stamp is either chemically modified or doped with particles or dye so that functional groups, molecules or particles provide different optical (or electrical) properties. A preferred added material is a fluorescent dye. A fluorescent nature can be imparted to the stamp through inclusion of interstitial fluorescent particles, dissolution of fluorescent compounds into the stamp, modification or design such that composition of the stamp is natively fluorescent, or any combination of the above.

The illumination of the image carrier with UV light can be done with a variety of schemata. The stamp may be illuminated with diffuse UV light having a wavelength appropriate to the emission spectra of the fluorescent markers in the stamp. The light is preferably directed at the region of contact to directly illuminate the contact region. The incident light can also be directionalized to fall incident on the contact region obliquely, as shown in FIGS. 1a and 1b, or in dark field illumination. The incident light can also be confined to the impression surface by utilizing frustrated total internal reflection such that the entrained light only falls incident on the regions of intimate contact and remains suitably entrained in the impression surface outside of the regions. The lighting can be any combination of the above.

Figure 2A:
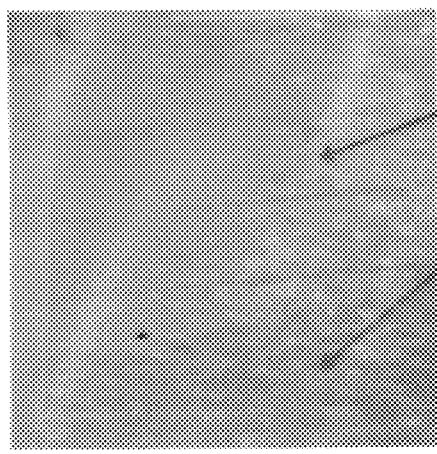
FIGS. 2a and 2b are acquired images from the embodiment illustrated in FIG. 1a showing regions where the stamp is in contact with the substrate and not in contact with the substrate.
Figure 2B:
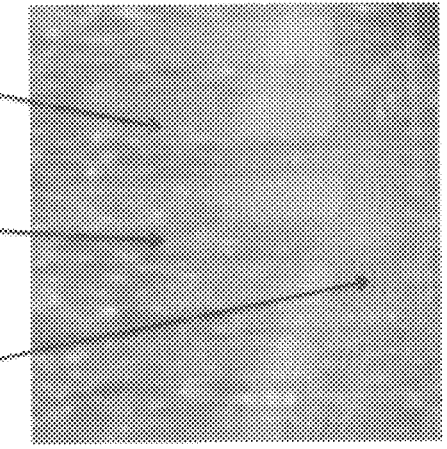

With reference now to FIGS. 2a and 2b, contact is detected by examining the brightness through a transparent substrate. As the stamp re-emits the incident UV light into the visible spectrum, there is a change in the optical impedance between the image carrier and the detector in the imaging system which is as a result of contact or no contact between the substrate and the impression system. FIGS. 2a and 2b show this sensing principle as areas of contact are highlighted against areas of no contact.

Figure 3A:
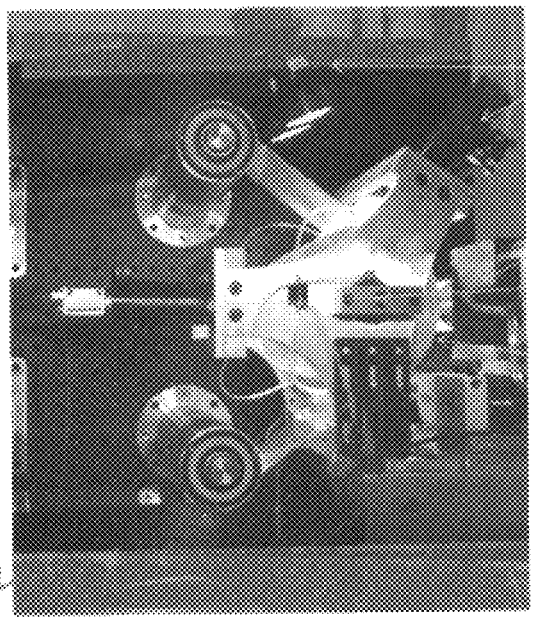
FIG. 3a is a photograph of an implementation of an embodiment of the invention disclosed herein in a roll-to-roll format.
Figure 3B:
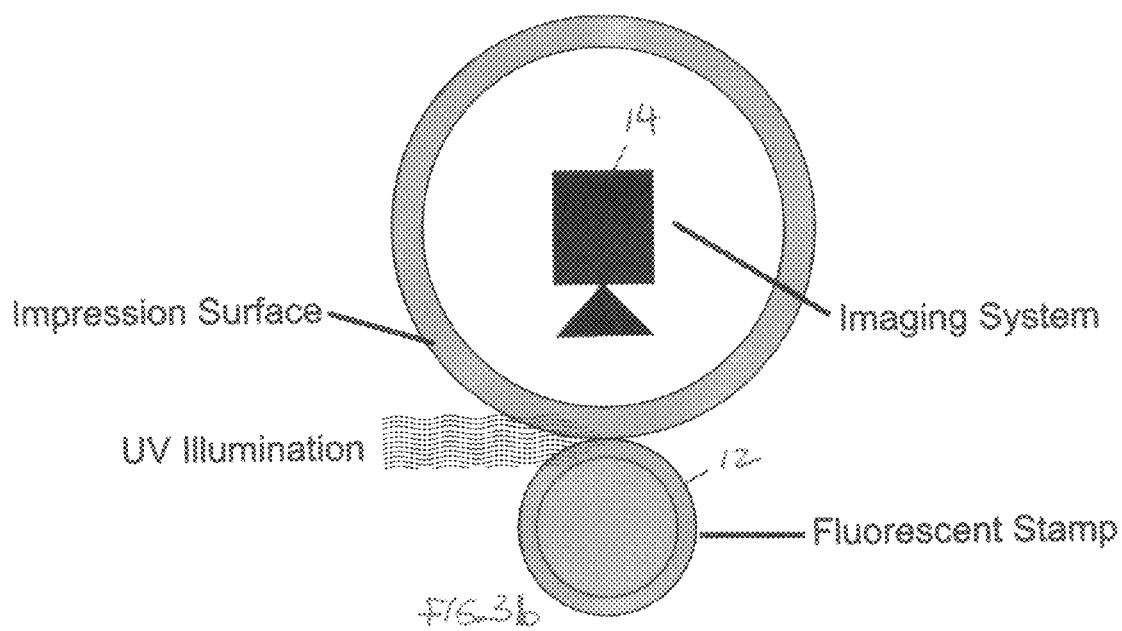
FIG. 3b is a schematic representation of the implementation of an embodiment of the invention disclosed herein in a roll-to-roll format demonstrating a cylindrical impression surface that is hollow.
Figure 3C:
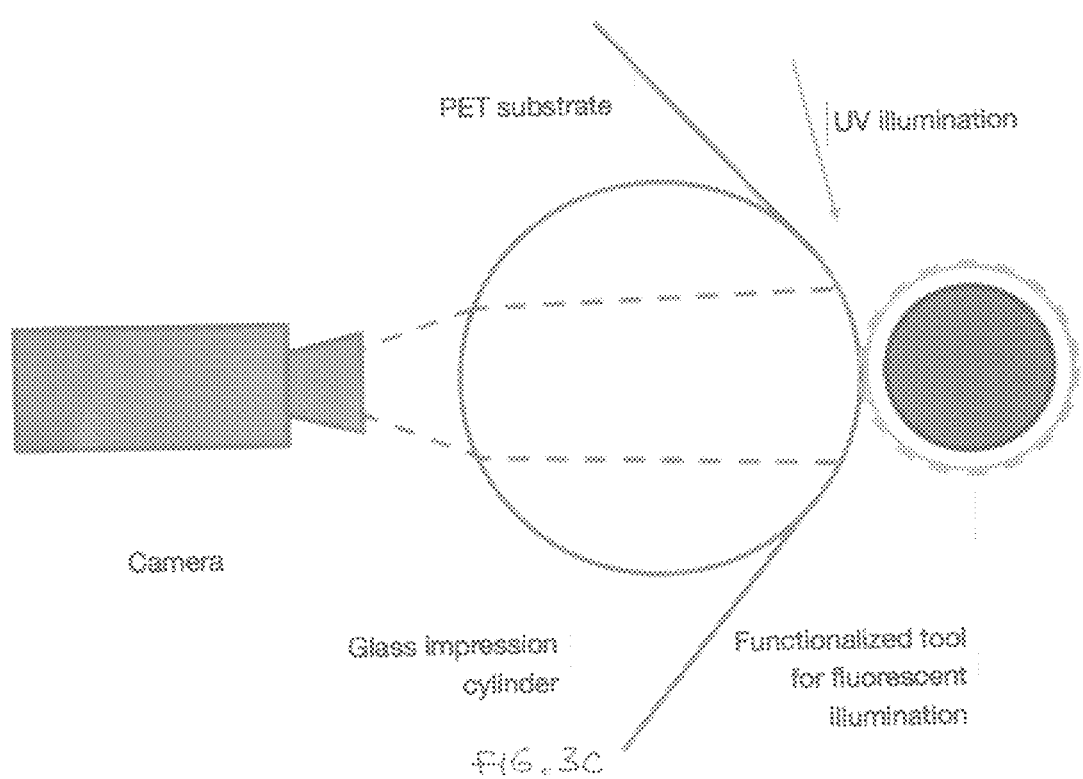
FIG. 3c is a schematic representation of the implementation of an embodiment of the invention disclosed herein in a roll-to-roll format demonstrating a cylindrical impression surface that is solid.

FIGS. 3a, 3b and 3c show embodiments of the invention in a roll-to-roll format. FIG. 3a shows the impression roll camera, image carrier and the UV illumination source. FIG. 3b shows an embodiment employing a cylindrical impression surface that is hollow. FIG. 3c illustrates a cylindrical impression surface that is solid.

Unlike binary contact imaging methods, the method utilized in the system of the invention can yield information beyond contact. In FIGS. 2a and 2b, interference patterns appear based on the proximity of the portion of the stamp out of contact. This can be used to very precisely measure the contact dynamics through interferometry. This example of measuring contact dynamics through interferometry is just one example of a myriad of sensing parameters that are possible. All additional data is collected from the same root image but separated in a computational post-processing.

The present invention has immediate application to the additive, continuous manufacturing industry in which the value of the process is high and there is a need to make very low defect patterns. The industry currently does not perform closed-loop control of the print contact because the sensing technology is unavailable. With the present invention, one is able to provide a sensor and thus enable closed-loop control as will be apparent to those of ordinary skill in the art.

The stamp can either be uniformly loaded with particles/dye, or contain multiple layers. In particular, a clear layer can contain the stamp features and an adjacent layer can contain the particles/dye.

While the invention has been described with respect to the use of UV light, it is noted that infrared (IR) light may also be used. In such an embodiment, the image carrier shall not be transparent to IR. In contrast to the previously described embodiments, the image carrier does not have to contain a fluorescein marker. The IR lighting can be incident on the contact region via any combination of the methods described above. The camera and imaging system must be appropriate for capturing light of an appropriate wavelength outside the visible spectrum in order that the IR image may be observed. If a substrate is used, it too shall have the appropriate optical characteristics as not to interfere with the sensing principle herein disclosed. It is further noted that visible light may be used, comprising one or multiple frequencies, in place of IR light. A suitable microscope for use in the invention is disclosed in U.S. Pat. No. 8,559,103. Optical fluorescence based chemical and biochemical sensors are disclosed in WO2013092766. The contents of these references are incorporated herein by reference.

It is recognized that modifications and variations of the invention disclosed herein will be apparent to those of ordinary skill in the art, and it is intended that all such modifications and variations be included within the scope of the appended claims.

What is claimed is:

1. System for visualization of conformal contact between a patterned stamp and a transparent impression surface comprising:
   a patterned stamp including a fluorescent structure for contact with the impression surface;
   a source of UV light for transmission through the transparent impression surface to interact with the fluorescent structure to generate visible light re-emitted by the fluorescent structure; and
   an imaging system for capturing the visible light to form a high-contrast image of an area of conformal contact between the patterned stamp and the impression surface.

2. The system of claim 1 wherein the high-contrast image comprises bright and dark regions representing contact and no contact respectively.

3. The system of claim 1 wherein the stamp has a layered configuration including fluorescent structures.

4. The system of claim 1 wherein the stamp includes embedded fluorescent structures.

5. The system of claim 1 wherein the fluorescent structure is fluorescein.

6. The system of claim 1 wherein the transparent impression surface is a cylinder, solid or hollow.

7. The system of claim 1 wherein the illumination is in the infrared spectrum and the patterned stamp need not fluoresce.

8. The system of claim 1 wherein the image contains interferometric data.

* * * * *